(12) United States Patent
Chan et al.

(10) Patent No.: US 11,970,576 B2
(45) Date of Patent: Apr. 30, 2024

(54) BETA-PEPTIDO SUGAR-COPOLYMER

(71) Applicant: NANYANG TECHNOLOGICAL UNIVERSITY, Singapore (SG)

(72) Inventors: Bee Eng Mary Chan, Singapore (SG); Yu Du, Singapore (SG); Rubi Zamudio Vazquez, Singapore (SG); Kaixi Zhang, Singapore (SG); Zhangyong Si, Singapore (SG); Yuguang Mu, Singapore (SG); Hongwei Duan, Singapore (SG)

(73) Assignee: NANYANG TECHNOLOGICAL UNIVERSITY, Singapore (SG)

( * ) Notice: Subject to any disclaimer, the term of this patent is extended or adjusted under 35 U.S.C. 154(b) by 1327 days.

(21) Appl. No.: 16/477,503

(22) PCT Filed: Jan. 12, 2018

(86) PCT No.: PCT/SG2018/050019
§ 371 (c)(1),
(2) Date: Jul. 11, 2019

(87) PCT Pub. No.: WO2018/132073
PCT Pub. Date: Jul. 19, 2018

(65) Prior Publication Data
US 2022/0332892 A1    Oct. 20, 2022

(30) Foreign Application Priority Data
Jan. 12, 2017  (SG) .......................... 10201700245R

(51) Int. Cl.
| | | |
|---|---|---|
| *C08G 69/40* | (2006.01) | |
| *A61K 31/787* | (2006.01) | |
| *A61P 17/02* | (2006.01) | |
| *A61P 31/04* | (2006.01) | |
| *C08G 69/22* | (2006.01) | |

(52) U.S. Cl.
CPC ............ *C08G 69/40* (2013.01); *A61K 31/787* (2013.01); *A61P 17/02* (2018.01); *A61P 31/04* (2018.01); *C08G 69/22* (2013.01)

(58) Field of Classification Search
CPC ........ A61P 17/02; A61P 31/04; A61K 31/787; C08G 69/22; C08G 69/40
See application file for complete search history.

(56) References Cited

PUBLICATIONS

Dane et al. "Synthetic Enantiopure Carbohydrate Polymers That Are Highly Soluble in Water and Noncytotoxic," ACS Macro Lett. 2013, 2, 887-890. (Year: 2013).*
P.W. Rabideau and Z. Marcinow. "Birch Reduction of Aromatic Compounds," Organic Reactions, 42, 1992, 117-136. (Year: 1992).*
Dane, et al. "Poly-amido-saccharides: Synthesis via Anionic Polymerization of a b-Lactam Sugar Monomer," Journal of the American Chemistry Society, Aug. 31, 2012, vol. 134, No. 39, 16255-16264. (Year: 2012).*
Zhang, et al. "Access to Poly—Peptides with Functionalized Side Chains and End Groups via Controlled Ring-Opening Polymerization of b-Lactams," Journal of the American Chemical Society, Jun. 1, 2009, vol. 131, No. 4, 1589-1597. (Year: 2009).*
Bommarius et al., "Cost-effective expression and purification of antimicrobial and host defense peptides in *Escherichia coli,*" *Peptides* 31:1957-1965, 2010.
Cabrele et al., "Peptides Containing β-Amino Acid Patterns: Challenges and Successes in Medicinal Chemistry," *J. Med. Chem.* 57:9718-9739, 2014.
Centers for Disease Control and Prevention, "Methicillin-Resistant *Stapylococcus aureus* Infections Among Competitive Sports Participants—Colorado, Indiana, Pennsylvania, and Los Angeles County, 2000-2003," *MMWR* 52(33):793-795, 2003 (5 pages).
Cheng at al., "Synthesis and Conformational Analysis of Optically Active Poly(β-peptides)," *Macromolecules* 34:5159-5174, 2001.
Chmielewski et al., "[2 + 2] Cycloaddition of trichloroacetyl isocyanate to glycals," *Carbohydrate Research* 167:143-152, 1987.
Dane et al., "Poly-amido-saccharides: Synthesis via Anionic Polymerization of a β-Lactam Sugar Monomer," *J. Am. Chem. Soc.* 134:16255-16264, 2012.
Dane et al., "Synthetic Enantiopure Carbohydrate Polymers That are Highly Soluble in Water and Noncytotoxic," *ACS Macro Lett.* 2:887-890, 2013.
Eldred et al., "Effects of Side Chain Configuration and Backbone Spacing on the Gene Delivery Properties of Lysine-Derived Cationic Polymers," *Bioconjugate Chem.* 16:694-699, 2005.
Fang et al., "The mechanism of action of ramoplanin and enduracidin," *Mol. BioSyst.* 2:69-76, 2006.
Guichard et al., "Preparation of N-Fmoc-Protected β²- and β³-Amino Acids and Their Use as Building Blocks for the Solid-Phase Synthesis of β-Peptides," *Helvetica Chimica Acta* 81:187-206, 1998.
Hancock et al., "Antimicrobial and host-defense peptides as new anti-infective therapeutic strategies," *Nature Biotechnology* 24(12):1551-1557, 2006.
Hsu et al., "The nisin-lipid II complex reveals a pyrophosphate cage that provides a blueprint for novel antibiotics," *Nature Structural & Molecular Biology* 11(10):963-967, 2004.

(Continued)

*Primary Examiner* — Michael P Cohen
(74) *Attorney, Agent, or Firm* — Seed IP Law Group LLP

(57) ABSTRACT

There is provided a β-peptido sugar-copolymer having the structure of formula (I) as defined herein, or a stereoisomer, a tautomer, an N-oxide, a hydrate, a solvate, or a salt thereof, or a mixture of the same. There is provided a process to make the β-peptido sugar-copolymer as defined herein. There are further provided medical applications of the β-peptido sugar-copolymer as defined herein. In a preferred embodiment, a block-like copolymer poly(amido-D-glucose)-block-poly-β-(L)-homolysine (PDGu-b-PBLK) synthesized via anionic ring-opening polymerization (ROP) demonstrates an antimicrobial efficacy, an enhanced selectivity towards different bacteria, biocompatibility vs. mammalian cells and spontaneous assembly.

20 Claims, 11 Drawing Sheets

(56) References Cited

PUBLICATIONS

Huang et al., "A Convenient Method for the Construction of β-lactam Compounds from β-Amino Acids using 2-Chloro-1-Methylpyridinium Iodide as Condensing Reagent," *Chemistry Letters*:1465-1466, 1984.

International Search Report and Written Opinion, for International Application No. PCT/SG2018/050019, dated Mar. 15, 2018, 11 pages.

King et al., "Emergence of Community-Acquired Methicillin-Resistant *Staphylococcus aureus* USA 300 Clone as the Predominant Cause of Skin and Soft-Tissue Infections," *Ann Intern Med 144*:309-317, 2006.

Ling et al., "A new antibiotic kills pathogens without detectable resistance," *Nature 517*:455-459, 2015 (19 pages).

Liu et al., "Nylon-3 Polymers with Selective Antifungal Activity," *J. Am. Chem. Soc. 135*:5270-5273, 2013.

Matsuzaki et al., "Control of cell selectivity of antimicrobial peptides," *Biochimica et Biophysica Acta 1788*:1687-1692, 2009.

Müller et al., "Synthesis of Fmoc-β-Homoamino Acids by Ultrasound-Promoted Wolff Rearrangement," *Synthesis* :837-841, 1998.

Münch et al., "Structural variations of the cell wall precursor lipid II in Gram-positive bacteria—Impact on binding and efficacy of antimicrobial peptides," *Biochimica et Biophysica Acta 1848*:3062-3071, 2015.

Porter et al., "Mimicry of Host-Defense Peptides by Unnatural Oligomers: Antimicrobial β-Peptides," *J. Am. Chem. Soc. 124*:7324-7330, 2002.

Porter et al., "Non-haemolytic β-amino-acid oligomers," *Nature 404*:565, 2000.

Raguse et al., "Structure-Activity Studies of 14-Helical Antimicrobial β-Peptides: Probing the Relationship between Conformational Stability and Antimicrobial Potency," *J. Am. Chem. Soc. 124*:12774-12785, 2002.

Reynolds, "Structure, Biochemistry and Mechanism of Action of Glycopeptide Antibiotics," *Eur. J. Clin. Microbiol. Infect. Dis. 8*(11):943-950, 1989.

Santos et al., "Recent Developments in Antimicrobial Polymers: A Review," *Materials 9*:599, 2016 (33 pages).

Schmitt et al., "Interplay among Folding, Sequence, and Lipophilicity in the Antibacterial and Hemolytic Activities of αβ-Peptides," *J. Am. Chem. Soc. 129*:417-428, 2007.

Schneider et al., "Plectasin, a Fungal Defensin, Targets the Bacterial Cell Wall Precursor Lipid II," *Science 328*(5982):1168-1172, 2010.

Steinstraesser et al., "Host Defense Peptides as Effector Molecules of the Innate Immune Response: A Sledgehammer for Drug Resistance?" *Int. J. Mol. Sci. 10*:3951-3970, 2009.

Svenson et al., "Antimicrobial Peptides with Stability toward Tryptic Degradation," *Biochemistry 47*:3777-3788, 2008.

Templer et al., "Bacterial Skin and Soft Tissue Infections," *Hospital Physician 26*:9-16, 2009.

Yeaman et al., "Mechanisms of Antimicrobial Peptide Action and Resistance," *Pharmacological Reviews 55*(1):27-55, 2003.

Zasloff, "Antimicrobial peptides of multicellular organisms," *Nature 415*:389-395, 2002.

Zhang et al., "Access to Poly-β-Peptides with Functionalized Side Chains and End Groups via Controlled Ring-Opening Polymerization of β-Lactams," *J. Am. Chem. Soc. 131*:1589-1597, 2009.

Zhang et al., "Kinetics of Anionic Ring-Opening Polymerization of Variously Substituted β-Lactams: Homopolymerization and Copolymerization," *Macromolecules 43*:5618-5626, 2010.

\* cited by examiner (b)

(c)

BETA-PEPTIDO SUGAR-COPOLYMER

CROSS-REFERENCE TO RELATED APPLICATION

This application claims the benefit of priority of Singapore patent application No. 10201700245R, filed Jan. 12, 2017, the content of which is incorporated herein by reference in its entirety for all purposes.

TECHNICAL FIELD

Various embodiments relate to a β-peptido sugar-copolymer, a process for making the β-peptido sugar-copolymer, and the medical application of the β-peptido sugar-copolymer as an antimicrobial.

BACKGROUND

Since the discovery of natural antimicrobial peptides (AMPs) in the 1980s, a lot of efforts have been made of these natural antimicrobial agents, synthetic peptide analogues and unnatural, sequence-specific oligomers for potential therapeutic applications. However, very little success has been achieved, as AMPs and their analogues are sensitive to physiological environment, toxic to host cells and expensive to obtain. It was previously thought that antimicrobial peptides kill bacteria by forming pores in the cytoplasmic membrane, until recently, when some of these may have been found to have specific targets. For example, plectasin-like defensins (and some human defensins to a lesser extent), lantibiotics (e.g. nisin), glycolipodepsipeptides (e.g. ramoplanin), glycopeptides (e.g. vancomycin) all act specifically on lipid II, a peptidoglycan precursor. These special classes of peptides have specific bindings with lipid II, particularly the glycol-based peptides/depsipeptides. The lantibiotics, ramoplanin and defensins bind to the pyrophosphate linkage of lipid II whilst vancomycin binds to the D-Alanine-D-Alanine tail of the peptide stem. However, some of these peptides have multiple targets. For example, nisin also destabilizes the membrane of the bacteria besides the binding to the pyrophosphate. Recently, Ling et al discovered teixobactin, which has good Gram-positive bacteria killing efficacy and no resistance evolution was reported, so that protein binding is not involved. It appears that teixobactin binds to the pyrophosphate-sugar moiety. It appears that multiple targets and cationic glycopeptides that target various moieties of lipid II seem to be a possible path forward.

In order to make up aforementioned innate drawbacks, research has focused on synthetic mimics of antimicrobial peptides (SMAMPs) in recent years. Poly-β-peptides derived from anionic ring-opening polymerization (ROP) of β-lactams have been developed as one class of attractive antimicrobial materials. Compared to α-peptides, β-peptides are known to form secondary structures such as alpha-helices or beta-sheets more easily, which lead to amphiphilic conformations that are crucial for antimicrobial application by suitable arrangement of β-amino acids. Furthermore, β-peptides are more stable towards enzymes in physiological environment. Gellman et al have extensively investigated homocationic beta-peptides but not the glycosylated version.

In view of the above, there exists a need for an improved copolymer that may be used as an antimicrobial that overcomes or at least alleviates one or more of the above problems.

SUMMARY

In a first aspect, a β-peptido sugar-copolymer is provided. The β-peptido sugar-copolymer has a Formula (I)

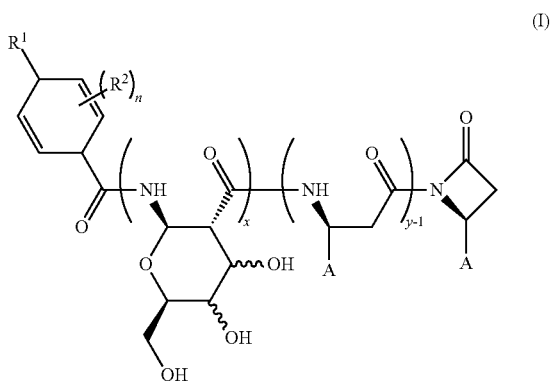

wherein:

A is selected from any amino acid residue;

x and y are independently selected from 1 to 50;

$R^1$ and $R^2$ are independently selected from the group consisting of H, halogen, a substituted or unsubstituted $C_1$-$C_{20}$ alkyl, a substituted or unsubstituted $C_1$-$C_{20}$ alkoxy, a substituted or unsubstituted $C_2$-$C_{20}$ alkenyl, a substituted or unsubstituted $C_2$-$C_{20}$ alkynyl, a substituted or unsubstituted $C_3$-$C_{20}$ alicyclic group, a substituted or unsubstituted $C_6$-$C_{15}$ aryl, a substituted or unsubstituted $C_7$-$C_{30}$ alkyl-aryl, a substituted or unsubstituted $C_3$-$C_{20}$ heterocycle, a substituted or unsubstituted $C_4$-$C_{30}$ alkyl-heterocycle, a substituted or unsubstituted $C_5$-$C_{15}$ heteroaryl; and n is an integer selected from 0 to 4;

or a stereoisomer, a tautomer, an N-oxide, a hydrate, a solvate, or a salt thereof, or a mixture of the same.

In a second aspect, a process for making a compound of Formula (I), or a stereoisomer, a tautomer, an N-oxide, a hydrate, a solvate, or a salt thereof, or a mixture of the same is provided. The process comprises a first step of reacting a compound of Formula (IV)

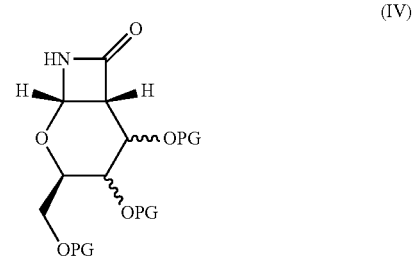

with a compound of formula (V)

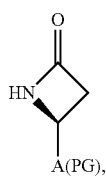

(V)

further comprising a compound of the following Formula (VI)

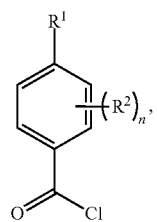

(VI)

to give a β-peptido sugar-copolymer of formula (VII)

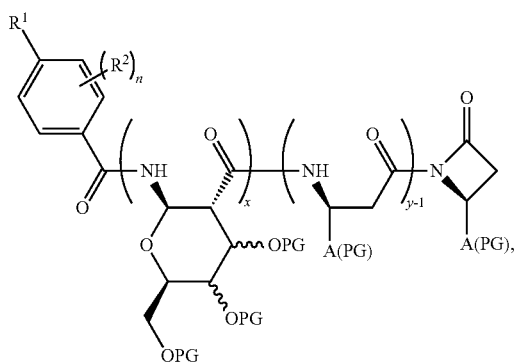

(VII)

further comprising at least one second step of deprotecting the β-peptido sugar-copolymer of Formula (VII) to give the β-peptido sugar-copolymer of Formula (I),

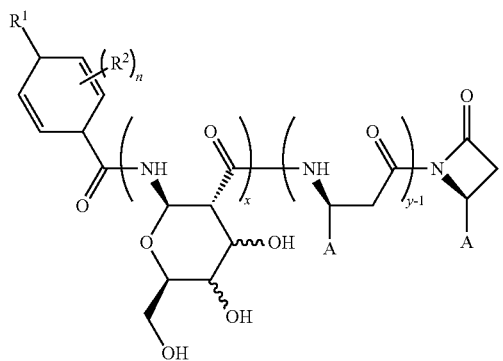

(I)

wherein PG refers to a protecting group, A(PG) refers to an optionally protected amino acid residue,
A is selected from any amino acid residue;
x and y are independently selected from 1 to 50;
$R^1$ and $R^2$ are independently selected from the group consisting of H, halogen, a substituted or unsubstituted $C_1$-$C_{20}$ alkyl, a substituted or unsubstituted $C_1$-$C_{20}$ alkoxy, a substituted or unsubstituted $C_2$-$C_{20}$ alkenyl, a substituted or unsubstituted $C_2$-$C_{20}$ alkynyl, a substituted or unsubstituted $C_3$-$C_{20}$ alicyclic group, a substituted or unsubstituted $C_6$-$C_{15}$ aryl, a substituted or unsubstituted $C_7$-$C_{30}$ alkyl-aryl, a substituted or unsubstituted $C_3$-$C_{20}$ heterocycle, a substituted or unsubstituted $C_4$-$C_{30}$ alkyl-heterocycle, a substituted or unsubstituted $C_5$-$C_{15}$ heteroaryl; and n is an integer selected from 0 to 4.

In a third aspect, a pharmaceutical composition comprising the β-peptido sugar-copolymer as described above is provided.

In a fourth aspect, a β-peptido sugar-copolymer as described above or the pharmaceutical composition as described above for use in therapy is provided.

In a fifth aspect, use of a β-peptido sugar-copolymer as described above or the pharmaceutical composition as described above in the manufacture of a medicament for the treatment of skin and soft tissue infections is provided.

In a sixth aspect, a method of treating skin and soft tissue infections comprising administering to a mammal a therapeutically effective amount of a β-peptido sugar-copolymer as described above or the pharmaceutical composition as described above is provided.

BRIEF DESCRIPTION OF THE DRAWINGS

The invention will be better understood with reference to the detailed description when considered in conjunction with the non-limiting examples and the accompanying drawings, in which.

DETAILED DESCRIPTION

Figure 1:
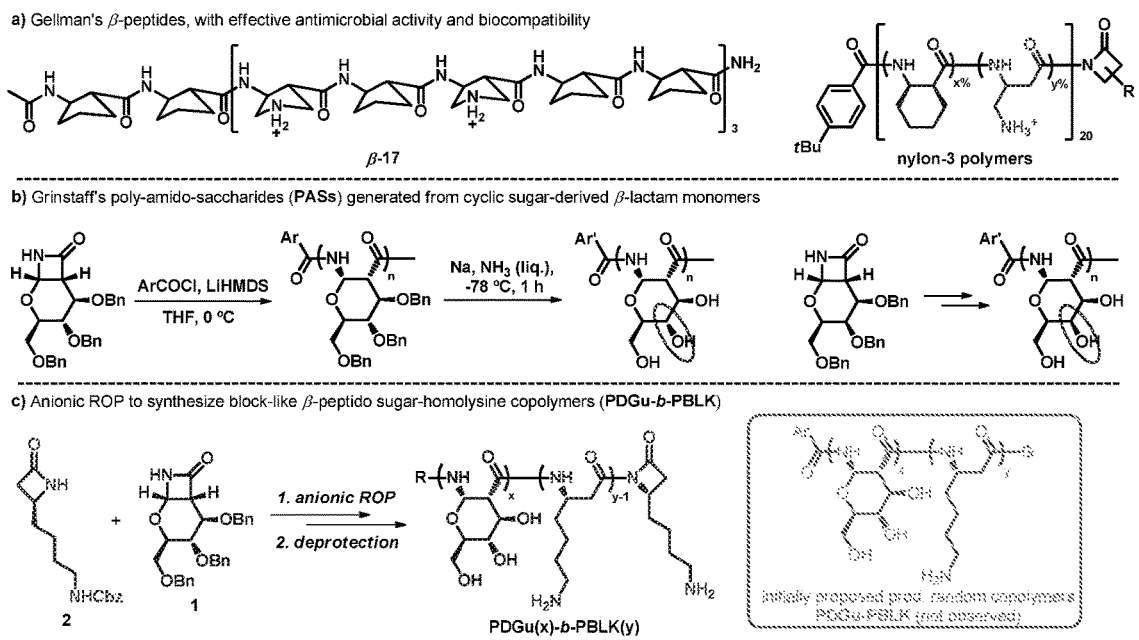
FIG. 1 shows the background and proposal to synthesize antibacterial β-Peptido sugar-copolymers via anionic ROP.

Various embodiments refer to β-peptido sugar-copolymers based on β-amino acids and sugar derivatives suitable for use as antimicrobials. The term "β-peptido sugar-copolymer" as used herein refers to a copolymer which is derived from a polymerisation reaction between a β-lactam monomer, which is a modified β-amino acid, and a cyclic sugar-derived β-lactam monomer. The copolymer may be a "block-like" copolymer. The term "block-like", as used herein, may refer to a copolymer, wherein each type of the reoccuring structural units is in sequence, as opposed to alternating. Hence, the block-like copolymer may comprise, or consist essentially of two blocks, wherein one block comprises the sugar-derived block and the other block comprises the β-(L)-homoamino acid derived-block. Advantageously, by being in a "block" sequence, the β-peptido sugar-copolymer may preserve the intrinisic properties of each block rather than the average properties observed with random copolymers. The β-peptido sugar-copolymer may show good antibacterial effect and no hemolysis against Gram-positive bacteria, even against Methicillin-resistant *Staphylococcus aureus* (MRSA, clinical resistant strains of *S. aureus*). Further advantageously, the sugar-derived block may provide good biocompatibility, while the β-(L)-homoamino acid-derived block may provide good antimicrobial activity, making the combination of both an excellent drug candidate. The secondary structures of the β-peptido sugar-copolymer may not only be derived from the chiral repeat units, but also by the strong inducing effect of helical poly-amido-D-pyranose units, resulting in double helical hydrophilic conformation which shows selectivity towards different bacteria, biocompatibility vs. mammalian cells, and spontaneous assembly in aqueous solution. The poly-β-(L)-homoamino acid-derived block may perform as the bacterial-killing block and forms a left-handed helical structure; the chiral D-pyranose derived block may also form secondary helical structures and may contribute to the binding of the β-peptido sugar-copolymer with a target of an antibiotic, such as lipid II.

With the above in mind, various embodiments refer in a first aspect to a β-peptido sugar-copolymer of Formula (I):

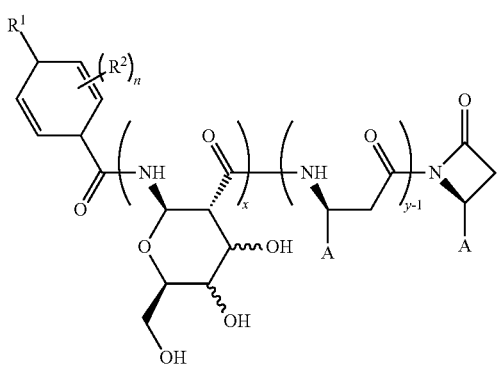

(I)

wherein:
A is selected from any amino acid residue;
x and y are independently selected from 1 to 50;
$R^1$ and $R^2$ are independently selected from the group consisting of H, halogen, a substituted or unsubstituted $C_1$-$C_{20}$ alkyl, a substituted or unsubstituted $C_1$-$C_{20}$ alkoxy, a substituted or unsubstituted $C_2$-$C_{20}$ alkenyl, a substituted or unsubstituted $C_2$-$C_{20}$ alkynyl, a substituted or unsubstituted $C_3$-$C_{20}$ alicyclic group, a substituted or unsubstituted $C_6$-$C_{15}$ aryl, a substituted or unsubstituted $C_7$-$C_{30}$ alkyl-aryl, a substituted or unsubstituted $C_3$-$C_{20}$ heterocycle, a substituted or unsubstituted $C_4$-$C_{30}$ alkyl-heterocycle, a substituted or unsubstituted $C_5$-$C_{15}$ heteroaryl; and n is an integer selected from 0 to 4;
or a stereoisomer, a tautomer, an N-oxide, a hydrate, a solvate, or a salt thereof, or a mixture of the same.

In the present context, the term "alkyl", alone or in combination, refers to a fully saturated aliphatic hydrocarbon. The alkyl may be linear or branched. In certain embodiments, alkyls are optionally substituted. In certain embodiments, an alkyl comprises 1 to 20 carbon atoms, for example 1 to 10 carbon atoms, wherein (whenever it appears herein in any of the definitions given below) a numerical range, such as "1 to 20" or "$C_1$-$C_{20}$", refers to each integer in the given range, e.g. "$C_1$-$C_{20}$ alkyl" means that an alkyl group comprising only 1 carbon atom, 2 carbon atoms, 3 carbon atoms, 4 carbon atoms, 5 carbon atoms, 6 carbon atoms, 7 carbon atoms, 8 carbon atoms, 9 carbon atoms, 10 carbon atoms, 11 carbon atoms, 12 carbon atoms, 13 carbon atoms, 14 carbon atoms, 15 carbon atoms, 16 carbon atoms, 17 carbon atoms, 18 carbon atoms, 19 carbon atoms, or 20 carbon atoms. Lower alkyl means 1 to 8, preferably 1 to 6, more preferably 1 to 4 carbon atoms.

Examples of the alkyl group include methyl, ethyl, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), and 1,1-dimethylethyl or t-butyl ("t-Bu"). Other examples of the alkyl group include 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl groups.

In the present context, the term "alkoxy", alone or in combination, refers to an aliphatic hydrocarbon having an alkyl-O-moiety. The alkoxy may be linear or branched. In certain embodiments, alkoxy groups are optionally substituted. In various embodiments, the alkoxy comprises 1 to 20 carbon atoms, i.e. $C_1$-$C_{20}$ alkoxy. Examples of alkoxy groups include, but are not limited to, methoxy, ethoxy, propoxy, butoxy and the like.

In the present context, the term "alkenyl", alone or in combination, refers to an aliphatic hydrocarbon having one or more carbon-carbon double-bonds, such as two or three carbon-carbon double-bonds. The alkenyl may be linear or branched. In certain embodiments, alkenyls are optionally substituted, i.e. substituted or unsubstituted. In certain embodiments, an alkenyl comprises 2 to 20 carbon atoms, such as 2 to 18, or 2 to 12, or 2 to 6 carbon atoms. "$C_2$-$C_{20}$ alkenyl" means that an alkenyl group comprising only 2 carbon atoms, 3 carbon atoms, 4 carbon atoms, 5 carbon atoms, 6 carbon atoms, 7 carbon atoms, 8 carbon atoms, 9 carbon atoms, 10 carbon atoms, 11 carbon atoms, 12 carbon atoms, 13 carbon atoms, 14 carbon atoms, 15 carbon atoms, 16 carbon atoms, 17 carbon atoms, 18 carbon atoms, 19 carbon atoms, or 20 carbon atoms. Lower alkenyl means 2 to 8, 2 to 6 or 2 to 4 carbon atoms. Examples of alkenyls include, but are not limited to, ethenyl, propenyl, butenyl, 1,4-butadienyl, pentenyl, hexenyl, 4-methylhex-1-enyl, 4-ethyl-2-methylhex-1-enyl and the like.

In the present context, the term "alkynyl", alone or in combination, refers to an aliphatic hydrocarbon having one or more carbon-carbon triple-bonds, such as two or three carbon-carbon triple-bonds. The alkynyl may be linear or branched. In certain embodiments, alkynyls are optionally substituted, i.e. substituted or unsubstituted. In certain embodiments, an alkynyl comprises 2 to 20 carbon atoms, such as 2 to 18, or 2 to 12, or 2 to 6 carbon atoms. "$C_2$-$C_{20}$ alkynyl" means that an alkynyl group comprising only 2 carbon atoms, 3 carbon atoms, 4 carbon atoms, 5 carbon atoms, 6 carbon atoms, 7 carbon atoms, 8 carbon atoms, 9 carbon atoms, 10 carbon atoms, 11 carbon atoms, 12 carbon atoms, 13 carbon atoms, 14 carbon atoms, 15 carbon atoms, 16 carbon atoms, 17 carbon atoms, 18 carbon atoms, 19 carbon atoms, or 20 carbon atoms. Lower alkynyl means 2 to 8, 2 to 6 or 2 to 4 carbon atoms. Examples of alkynyls include, but are not limited to, ethynyl, propynyl, butynyl, and the like.

In the present context, the term "non-aromatic ring" refers to a group comprising a covalently closed ring that is not aromatic. The term "alicyclic" refers to a group comprising a non-aromatic ring wherein each of the atoms forming the ring is a carbon atom, and may be further classified into monocyclic and polycyclic (e.g., bicyclic and tricyclic) groups. Alicyclic groups may be formed of 3 to 20, or 3 to 12, or 3 to 8, or 3 to 6 carbon atoms, such as three, four, five, six, seven, eight, nine, or more than nine carbon atoms. In certain embodiments, alicyclics are optionally substituted, i.e. substituted or unsubstituted. In certain embodiments, an alicyclic comprises one or more unsaturated bonds, such as one or more carbon-carbon double-bonds. Alicyclics include cycloalkyls and cycloalkenyls. Examples of alicyclics include, but are not limited to, cyclopropane, cyclobutane, cyclopentane, cyclopentene, cyclopentadiene, cyclohexane, cyclohexene, 1,3-cyclohexadiene, 1,4-cyclohexadiene, cycloheptane, and cycloheptene.

In the present context, the term "aryl" refers to an aromatic ring wherein each of the atoms forming the ring is a carbon atom. Aryl rings may be formed by six, seven, eight, nine, or more than nine carbon atoms. Aryl groups may be optionally substituted. For example, an aryl group may be a 6-membered carbocyclic aromatic ring, such as, phenyl; bicyclic ring systems such as 7-12 membered bicyclic ring systems wherein at least one ring is carbocyclic and aromatic, selected, for example, from naphthalene, indane, and 1,2,3,4-tetrahydroquinoline; and tricyclic ring systems such as 10-15 membered tricyclic ring systems wherein at least one ring is carbocyclic and aromatic.

The term "alkyl aryl", as used herein, generally refers to a chemical substituent containing an alkyl group coupled to an aryl group or a substituted aryl group. The terms "aralkyl" and "aryl alkyl," as used alone or in combination herein, are species of alkyl as defined herein, and particularly refer to an alkyl group as defined above in which one hydrogen atom is replaced by an aryl group as defined above.

The terms "heterocyclic" or "heterocycle" or "heterocyclyl", as interchangeably used herein, refer to a ring selected from 4- to 12-membered monocyclic, bicyclic and tricyclic, saturated and partially unsaturated rings comprising at least one carbon atom in addition to 1, 2, 3 or 4 heteroatoms, selected from oxygen, sulfur, and nitrogen. "Heterocycle" also refers to a 5- to 7-membered heterocyclic ring comprising at least one heteroatom selected from N, O, and S fused with 5-, 6-, and/or 7-membered cycloalkyl, carbocyclic aromatic or heteroaromatic ring, provided that the point of attachment is at the heterocyclic ring when the heterocyclic ring is fused with a carbocyclic aromatic or a heteroaromatic ring, and that the point of attachment can be at the cycloalkyl or heterocyclic ring when the heterocyclic ring is fused with cycloalkyl.

"Heterocycle" also refers to an aliphatic spirocyclic ring comprising at least one heteroatom selected from N, O, and S, provided that the point of attachment is at the heterocyclic ring. The rings may be saturated or have at least one double bond (i.e. partially unsaturated). The heterocycle may be substituted with oxo. The point of the attachment may be carbon or heteroatom in the heterocyclic ring. A heterocyle is not a heteroaryl as defined herein. Examples of the heterocycle include, but not limited to, (as numbered from the linkage position assigned priority 1) 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, 2,5-piperazinyl, pyranyl, 2-morpholinyl, 3-mo holinyl, oxiranyl, aziridinyl, fhiiranyl, azetidinyl, oxetanyl, thietanyl, 1,2-dithietanyl, 1,3-difhietanyl, dihydropyridinyl, tetrahydropyridinyl, thiomorpholinyl, thioxanyl, piperazinyl, homopiperazinyl, homopiperidinyl, azepanyl, oxepanyl, thiepanyl, 1,4-oxathianyl, 1,4-dioxepanyl, 1,4-oxafhiepanyl, 1,4-oxaazepanyl, 1,4-difhiepanyl, 1,4-fhiazepanyl and 1,4-diazepane 1,4-dithianyl, 1,4-azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1,4-dioxanyl, 1,3-dioxolanyl, pyrazolinyl, pyrazolidinyl, dithianyl, difhiolanyl, pyrazolidinylimidazolinyl, pyrimidinonyl, 1,1-dioxo-thiomo holinyl, 3-azabicyco[3.1.0]hexanyl, 3-azabicyclo[4.1.0]heptanyl and azabicyclo[2.2.2]hexanyl.

The term "alkyl heterocycle", as used herein, generally refers to a chemical substituent containing an alkyl group coupled to a heterocycle or a substituted heterocycle.

In the present context, the term "heteroaryl" refers to an aromatic heterocycle. Heteroaryl rings may be formed by five, six, seven, eight, nine, or more than nine atoms. Heteroaryls may be optionally substituted. Examples of heteroaryl groups include, but are not limited to, aromatic $C_5$-$C_{15}$ heterocyclic groups comprising one oxygen or sulfur atom or up to four nitrogen atoms, or a combination of one oxygen or sulfur atom and up to two nitrogen atoms, and their substituted as well as benzo- and pyrido-fused derivatives, for example, connected via one of the ring-forming carbon atoms.

In various embodiments, the molecular weight of the β-peptido sugar-copolymer may be between 1 and 20 kDa, or between 1 and 15 kDa, or between 1 and 10 kDa, or between 5 and 20 kDa, or between 5 and 10 kDa, or between 6 and 9 kDa.

In various embodiments, A may be an amino acid residue. For example, A may be derived from an amino acid selected from the group consisting of alanine (Ala), valine (Val), leucine (Leu), phenylalanine (Phe), tyrosine (Tyr), isoleucine (Ile), asparagine (Asn), glutamine (Gln), serine (Ser), threonine (Thr), cysteine (Cys), methionine (Met), tryptophan (Trp), aspartate (Asp), histidine (His), lysine (Lys), arginine (Arg) and glutamate (Glu). Accordingly, A may be selected from the group consisting of —$CH_3$ (Ala), —CH($CH_3$)$_2$ (Val), —$CH_2$CH($CH_3$)$_2$ (Leu), —$CH_2$Ph (Phe), —CH($CH_3$)$CH_2$$CH_3$ (Ile), —$CH_2$C(O)$NH_2$ (Asn), —$CH_2$$CH_2$C(O)$NH_2$ (Gln), —$CH_2$OH (Ser), —CHCH$_3$OH (Thr), —$CH_2$SH (Cys), —$CH_2$$CH_2$S$CH_3$ (Met),

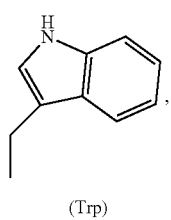

(Trp)

—CH$_2$(p-hydroxy)Ph (Tyr), —CH$_2$COOH (Asp),

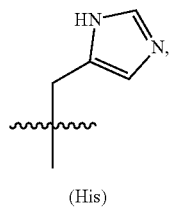 [SMILES: *Cc1cnc[nH]1]

(His)

—(CH$_2$)$_4$—NH$_2$ (Lys), —(CH$_2$)$_3$NHC(NH)NH$_2$ (Arg) and —CH$_2$CH$_2$COOH (Glu), where the content in the parenthesis denotes the amino acid from which the functional group is derived from. Protonated or deprotonated modifications of the amino acid residues are included in this definition.

The β-peptido sugar-copolymer may be present as a tautomer, for example, in case the amino acid residue is a histidine residue. Hence, the present disclosure includes all possible tautomers of the β-peptido sugar-copolymer of the present disclosure as single tautomers, or as any mixture of said tautomers, in any ratio. Further, the β-peptido sugar-copolymer of the present disclosure can exist as N oxides, which are defined in that at least one nitrogen of the compounds of the present disclosure is oxidised. The present disclosure includes all such possible N oxides. The present disclosure also relates to useful forms of the β-peptido sugar-copolymer as disclosed herein, such as hydrates, solvates, salts, in particular pharmaceutically acceptable salts. The β-peptido sugar-copolymer of the present disclosure can exist as a hydrate, or as a solvate, wherein the β-peptido sugar-copolymer of the present invention contain polar solvents, in particular water, methanol or ethanol. The amount of polar solvents, in particular water, may exist in a stoichiometric or non-stoichiometric ratio. Further, the compounds of the present disclosure can exist in free form, e.g. as a free base, or as a free acid, or as a zwitterion, or can exist in the form of a salt. Said salt may be any salt, either an organic or inorganic addition salt, particularly any pharmaceutically acceptable organic or inorganic addition salt, customarily used in pharmacy.

The term "pharmaceutically acceptable salt" refers to a relatively non toxic, inorganic or organic acid addition salt of a compound of the present disclosure. For example, see S. M. Berge, et al. "Pharmaceutical Salts," J. Pharm. Sci. 1977, 66, 1 19. A suitable pharmaceutically acceptable salt of the compounds of the present disclosure may be, for example, an acid addition salt of a compound of the present disclosure bearing a nitrogen atom, in a chain or in a ring, for example, which is sufficiently basic, such as an acid addition salt with an inorganic acid, such as hydrochloric, hydrobromic, hydroiodic, for example, or with an organic acid, such as formic, acetic, acetoacetic, trifluoroacetic, trifluoromethanesulfonic, para toluenesulfonic, methanesulfonic, for example.

Those skilled in the art will further recognise that acid addition salts of the claimed compounds may be prepared by reaction of the compounds with the appropriate inorganic or organic acid via any of a number of known methods. The present disclosure includes all possible salts of the compounds of the present invention as single salts, or as any mixture of said salts, in any ratio.

In various embodiments, A may be derived from a basic amino acid. A basic amino acid may be histidine, lysine and arginine.

In specific embodiments, A is —(CH$_2$)$_4$—NH$_2$ (Lys).

The β-peptido sugar-copolymer may have a component which is derived from a pyranose (shown as the pyran moiety in Formula (I)). The pyranose from which the β-peptido sugar-copolymer is derived may be selected from D-allose, D-altrose, D-galactose, D-glucose, D-gulose, D-idose, D-mannose and D-talose.

Preferably, the β-peptido sugar-copolymer may be derived from D-allose, D-altrose, D-glucose and D-mannose. The before mentioned pyranoses all share the common feature that the hydroxyl group adjacent to the carbon bearing the methyl-hydroxy moiety is in the (S)-configuration. Hence, these β-peptido sugar-copolymers may have the following structure of formula (II):

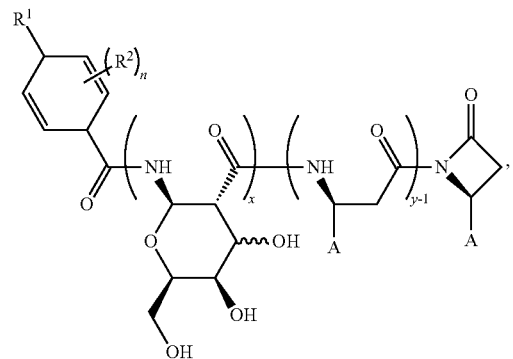

(II)

wherein R$^1$, R$^2$, A, n, x and y are as defined above,
or a stereoisomer, a tautomer, an N-oxide, a hydrate, a solvate, or a salt thereof, or a mixture of the same.

In one example, the pyranose from which the β-peptido sugar-copolymer is derived may be D-glucose. Hence, these β-peptido sugar-copolymers may have the following structure of formula (III):

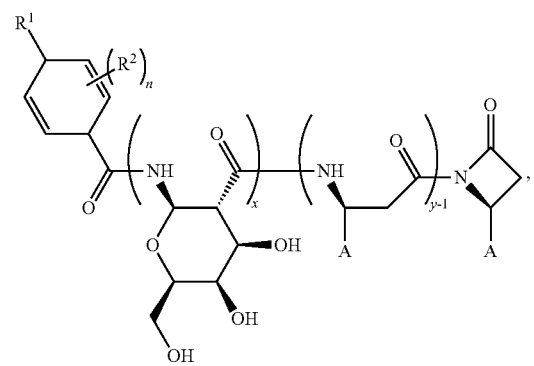

(III)

wherein $R^1$, $R^2$, A, n, x and y are as defined above, or a stereoisomer, a tautomer, an N-oxide, a hydrate, a solvate, or a salt thereof, or a mixture of the same.

In various embodiments, the block sizes of the β-peptido sugar-copolymer may be selected such that x and y are independently selected from 1 to 20. The values x and y may not refer to actual integers, but may express an average value for the block sizes, depending on the synthetic protocol. In various embodiments, x and y may be independently selected from 5 to 15.

In various embodiments, the block sizes of the β-peptido sugar-copolymer may be selected such that the sum of x and y equals 20. In alternative embodiments, the block sizes of the β-peptido sugar-copolymer may be selected such that the sum of x and y in the obtained copolymer equals 15. In one example, x and y are both 10. In another example, x is about 5 and y is about 10. In another example, y is about twice as much as x, including a 10% deviation. While the block sizes may be varied depending on the ratios used during synthesis, the ultimate block sizes obtained may differ from the ratios utilized during synthesis.

In various embodiments, $R^1$ may be selected from a substituted or unsubstituted $C_1$-$C_{20}$ alkyl. $R^1$ being an alkyl chain may be particularly advantageous in the undertaking of the Birch reaction as described below, as it provides a stabilizing effect to the reaction. In various preferred embodiments, $R^1$ may be selected from an unsubstituted, branched $C_3$-$C_5$ alkyl. In one example, $R^1$ is t-butyl.

The β-peptido moiety of the β-peptido sugar-copolymer may adopt a left-handed helical structure. This may be due to the chirality of the β-peptide structure, which is inherently left-handed. It may also be due to the cationic nature, in case a basic (and protonated) amino acid residue is used, such as a protonated lysine residue. The cation may be located at the electron-rich nitrogen of the basic amino acid residue.

The sugar moiety of the β-peptido sugar-copolymer may form a secondary helical structure, such as a right-handed helical structure. This may be due to the sugar backbone, which is inherently right-handed.

The β-peptido sugar-copolymer, comprising the β-peptido moiety as well as the sugar moiety, may adopt a sequential double helix structure.

In a second aspect, there is provided a process for making a compound of Formula (I), or a stereoisomer, a tautomer, an N-oxide, a hydrate, a solvate, or a salt thereof, or a mixture of the same. The process may comprise a first step of reacting a cyclic sugar derived β-lactam monomer of Formula (IV)

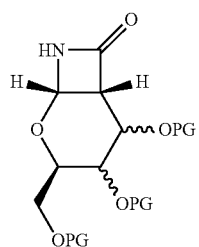
(IV)

with a β-lactam monomer of formula (V)

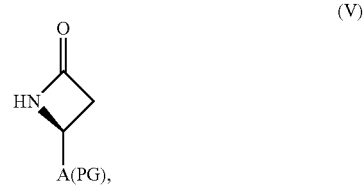
(V)

further comprising a compound of the following Formula (VI)

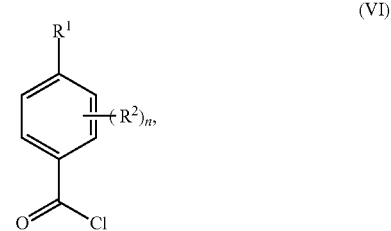
(VI)

to give a β-peptido sugar-copolymer of formula (VII)

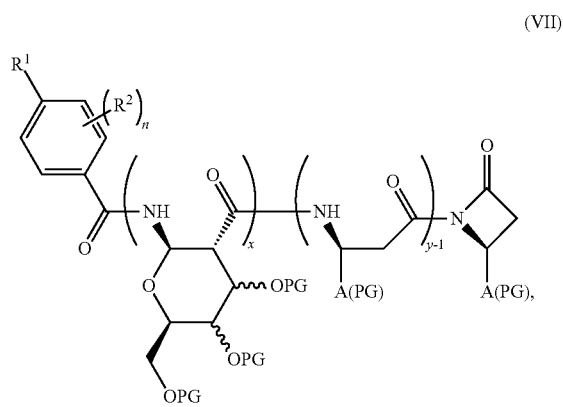
(VII)

further comprising at least one second step of deprotecting the β-peptido sugar-copolymer of Formula (VII) to give the β-peptido sugar-copolymer of Formula (I),

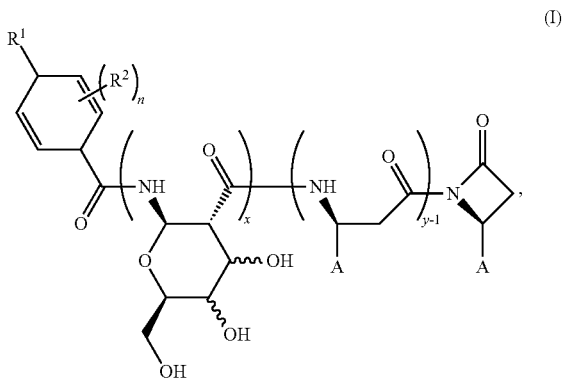
(I)

wherein PG may refer to a protecting group, A(PG) may refer to an optionally protected amino acid residue and A is selected from any amino acid residue;

x and y are independently selected from 1 to 50;

$R^1$ and $R^2$ are independently selected from the group consisting of H, halogen, a substituted or unsubstituted $C_1$-$C_{20}$ alkyl, a substituted or unsubstituted $C_1$-$C_{20}$ alkoxy, a substituted or unsubstituted $C_2$-$C_{20}$ alkenyl, a substituted or unsubstituted $C_2$-$C_{20}$ alkynyl, a substituted or unsubstituted $C_3$-$C_{20}$ alicyclic group, a substituted or unsubstituted $C_6$-$C_{15}$ aryl, a substituted or unsubstituted $C_7$-$C_{30}$ alkyl-aryl, a substituted or unsubstituted $C_3$-$C_{20}$ heterocycle, a substituted or unsubstituted $C_4$-$C_{30}$ alkyl-heterocycle, a substituted or unsubstituted $C_5$-$C_{15}$ heteroaryl; and n is an integer selected from 0 to 4.

The reaction of the first step may be termed an anionic ring-opening polymerization (ROP) of β-lactams.

The term "protecting group" as used herein may refer to a species which prevents a portion of a molecule from undergoing a specific chemical reaction, but which is removable from the molecule following completion of that reaction. A "protecting group" is used in the conventional chemical sense as a group which reversibly renders unreactive a functional group under certain conditions of a desired reaction, as taught, for example, in Greene, et al., "Protective Groups in Organic Synthesis," John Wiley and Sons, Second Edition, 1991. After the desired reaction, protecting groups may be removed to deprotect the protected functional group. All protecting groups should be removable (and hence, labile) under conditions which do not degrade a substantial proportion of the molecules being synthesized. In contrast to a protecting group, a "capping group" permanently binds to a segment of a molecule to prevent any further chemical transformation of that segment. It should be noted that the functionality protected by the protecting group may or may not be a part of what is referred to as the protecting group.

A protecting group in the context of the present invention may be a "hydroxyl protecting group" or "O-protecting group". Such a protecting group may refer to a protecting group where the protected group is a hydroxyl. A suitable O-protecting group may be selected from the group consisting of a methoxymethyl ether (MOM-OR), a tetrahydropyranyl ether (THP-OR), a t-Butyl ether, an allyl ether and a benzyl ether. The hydroxyl protecting group may be located on the hydroxyl groups pendant on the sugar-derived block. In one example, the protecting group is a benzyl ether. 'PG' in this example would then be —OBn.

Another protecting group in the context of the present invention may be an "amino protecting group", or "NH-protecting group". Such a protecting group may refer to a protecting group where the protected group is an amine. A suitable NH-protecting group may be selected from the group consisting of a 9-fluorenylmethyl carbamate (Fmoc-NRR'), a t-butyl carbamate (Boc-NRR'), a trifluoroacetamide, a benzyl carbamate (Z—NRR', Cbz-NRR'), a phthalimide, a benzylamine (Bn-NRR'), a triphenylmethylamine (Tr-NRR'), a benzylideneamine and a p-toluenesulfonamide (Ts-NRR'). The amino protecting group may be located on the amino acid-derived block. In one example, the amine protecting group is a benzyl carbamate (Z—NRR', Cbz-NRR') and protects the amino functionality of an amino acid residue. 'PG' in this example would then be —CBz.

In various embodiments, the reaction of the first step may involve a base. The base used in accordance with the present invention contains one or more nitrogen atom(s). The base used can be any suitable base and may, for example, be selected from the group consisting of pyrrolidine; $N(CH_3)_3$; $N(CH_2CH_3)_3$; (iso-Propyl)$_2$NH; 2,2,6,6-Tetramethyl-1-piperidin; LDA (Lithium diisopropylamid); LiHMDS (Lithium bis(trimethylsilyl)amide); LiTMP (Lithium tetramethylpiperidide); and 4-aminopyridine. In one example, the base is LiHMDS.

In various embodiments, the reaction of the first step may further be carried out in the presence of a solvent. Suitable solvents for this reaction may be selected from non-polar solvents, such as cyclopentane, hexane, cyclohexane, benzene, toluene, 1,4-dioxane, chloroform, diethyl ether or dichloromethane. Alternatively, the solvent may be selected from polar, protic solvents, such as acids, alcohols, nitromethane, water, and a combination thereof. Alternatively, the solvent may be selected from polar aprotic solvents, such as tetrahydrofuran, ethyl acetate, acetone, dimethylformamide, acetonitrile, dimethyl sulfoxide, nitromethane or propylene carbonate. In one example, the solvent is tetrahydrofuran.

In various embodiments, the reaction temperature used in the first step of the process disclosed herein ranges from −100° C. to 20° C. The reaction temperature of this step can also be from −50° C. to 0° C. Preferably, the reaction temperature used in the first step is about −30° C. to −15° C.

The process may comprise at least one second step. The at least one second step may be a deprotection step. This step may be a deprotection of the β-peptido sugar-copolymer of Formula (VII) to give the β-peptido sugar-copolymer of Formula (I), or a stereoisomer, a tautomer, an N-oxide, a hydrate, a solvate, or a salt thereof, or a mixture of the same.

The deprotection may be carried out under 'Birch conditions'. Hence, the reaction may involve an elemental alkali metal. Preferably, the elemental alkali metal is sodium. The reaction may further comprise a nitrogen base. Preferably, the nitrogen base is ammonia. The reaction temperature used in the deprotection step of the process disclosed herein ranges from −150° C. to 20° C. The reaction temperature of this step can also be from −100° C. to 0° C. Preferably, the reaction temperature used in the deprotection step may be from about −80° C. to about −50° C., more preferably from about −78° C. to about −55° C. Variations of these temperature ranges may be adjusted, depending on the structure of the starting material.

All protecting groups of the β-peptido sugar-copolymer of Formula (VII) may be cleaved in one step, which may be the at least one second step. The term "one step" as used herein means that the second step according to the present invention is carried out in the same reaction vessel without any purification step of an intermediate. Advantageously, this improves synthetic efficiency.

The deprotection of all protecting groups in one step may require the protecting groups to be deprotected simultaneously. The term "deprotecting simultaneously" may refer to a process which aims at removing different protecting groups in the same process and performed substantially concurrently or concurrently. However, as used herein, this term does not imply that the deprotection of the different protecting groups occur at exactly the same time or with the same rate or same kinetics.

In a third aspect, there is provided a pharmaceutical composition, comprising the β-peptido sugar-copolymer as described above.

In a fourth aspect, there is provided a β-peptido sugar-copolymer as described above or the pharmaceutical composition as described above for use in therapy.

In a fifth aspect, there is provided use of a β-peptido sugar-copolymer as described above or the pharmaceutical composition as described above in the manufacture of a medicament for the treatment of skin and soft tissue infections.

The β-peptido sugar-copolymer as described above or the pharmaceutical composition as described above may be administered at a daily dosage of between 10 mg and 500 mg, or between 50 mg and 500 mg, or between 100 mg and 500 mg, or between 10 mg and 300 mg, or between 10 mg and 200 mg, or between 50 mg and 200 mg, or between 50 mg and 100 mg, or at about 150 mg.

In a sixth aspect, there is provided a method of treating skin and soft tissue infections comprising administering to a mammal a therapeutically effective amount of a β-peptido sugar-copolymer as described above or the pharmaceutical composition as described above.

In various embodiments, the mammal may be a human.

The therapeutically effective amount may be between 10 mg and 500 mg, or between 50 mg and 500 mg, or between 100 mg and 500 mg, or between 10 mg and 300 mg, or between 10 mg and 200 mg, or between 50 mg and 200 mg, or between 50 mg and 100 mg, or at about 150 mg per day.

Figure 3A:
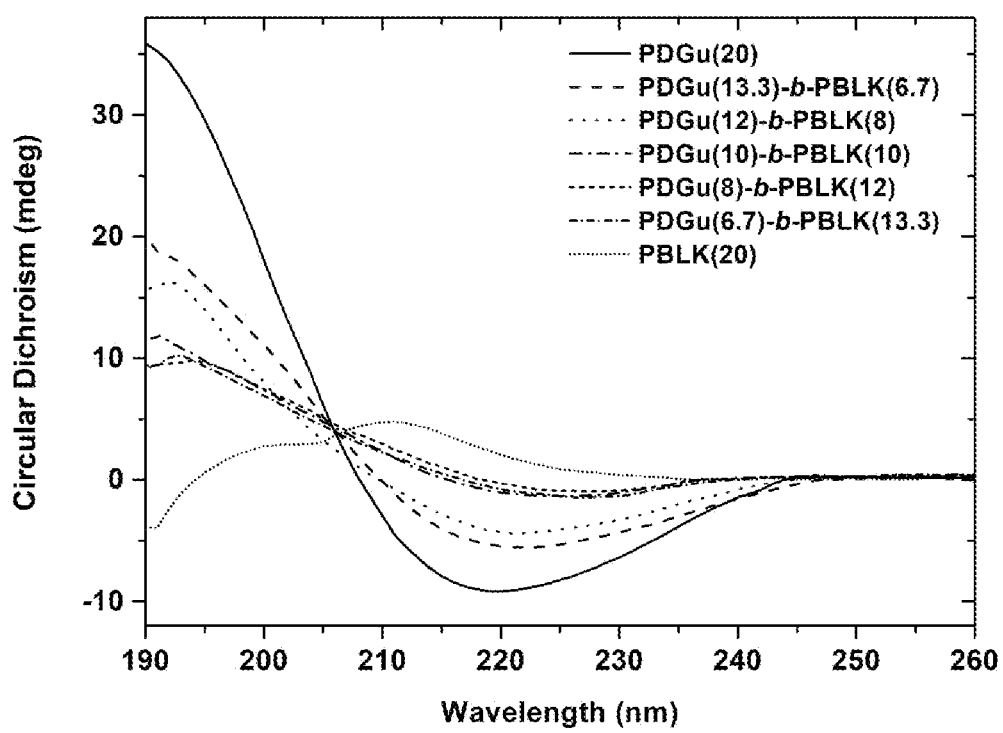
FIG. 3 shows (a) CD spectrums of homopolymer and PDGu-b-PBLK in deionized water. Sample concentration is 0.05 mg/ml. (b) Molecular modeling results of PDGu(12)-b-PBLK(12) (blk12-12), with PBLK forming a 12-helix. (c) Molecular modeling results of PDGu(12)-b-PBLK(14) (blk12-14), with PBLK forming a 14-helix.
Figure 3:
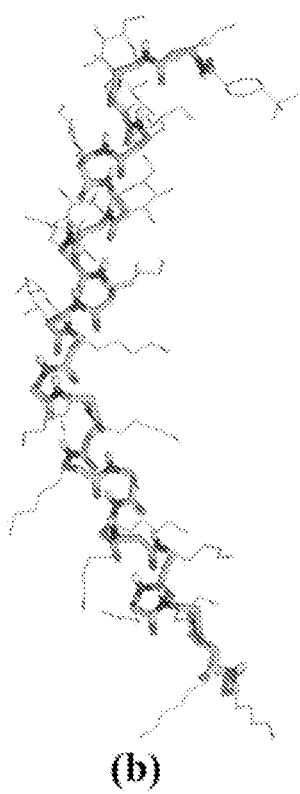
Figure 3:
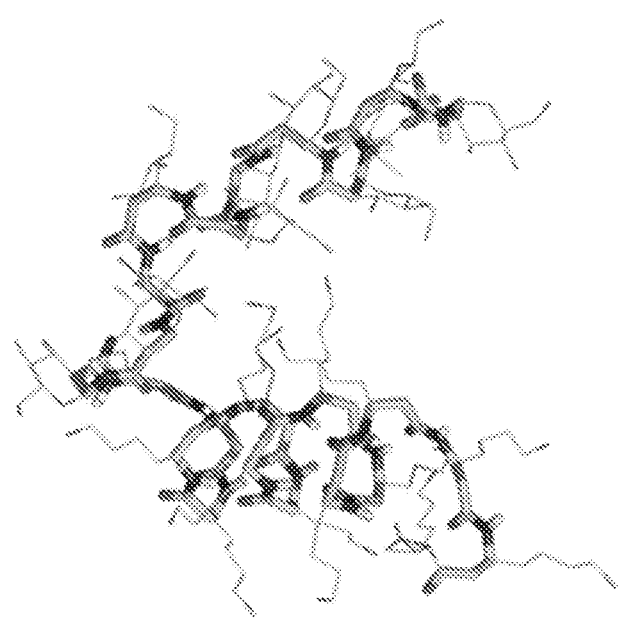

Herein is reported the first anionic ROP to synthesize in one step helical block-like β-peptido sugar-homolysine copolymers that show good antibacterial effect and no hemolysis. It is shown for the first time a poly-β-(L)-homolysine (PBLK) based block-like copolymer that has double helices and good antibacterial effect against Gram-positive bacteria, even Methicillin-resistant *Staphylococcus aureus* (MRSA, clinical resistant strains of *S. aureus*). Also, the secondary structures of the deprotected block-like copolymer is not only derived from the chiral repeat units, but also by the strong inducing effect of helical poly-amido-D-glucose (PDGu), resulting in double helical hydrophilic conformation which shows selectivity towards different bacteria, biocompatibility vs mammalian cells, and spontaneous assembly in aqueous solution (FIG. 3).

Gellman et al. first reported magainin mimic antimicrobial β-peptides (β-17, FIG. 1a) with excellent activity against a panel of pathogens. A family of random nylon-3 (β-peptides) polymers (FIG. 1a) was prepared through anionic ROP, which showed highly effective antimicrobial activity and biocompatibility. Grinstaff reported the synthesis of non-cytotoxic glucose/galactose type poly-amido-saccharides (PASs) through controlled anionic ROP, replacing the ether linkage found in natural polysaccharides with an amide linkage (FIG. 1b). However, glyco-β-peptides with the potential of more targeted bacteria binding and in vivo Multi-Drug Resistant (MDR) Gram-positive bacteria killing have not yet been reported. Based on this background, the synthetic strategy is illustrated in FIG. 1c. The initial attempt was to synthesize random copolymers composed of PBLK and PDGu by the reaction of monomers 1 and 2. Surprisingly, block-like copolymers were generated after reaction due to the large reactivity difference of the two monomers. One significant advantage in the synthetic procedure lies in the deprotection of both hydroxyl and amine groups to provide the final water-soluble products (PDGu-b-PBLK) in one step, which obviously improves the synthetic efficiency.

There is developed a new strategy to synthesize novel glyco-β-peptide-based polymers in one pot. This is the first anionic ROP that can synthesize block-like copolymers of polyamidosaccharide-block-β-peptide, specifically poly (amido-D-glucose)-block-poly-β-(L)-homolysine (PDGu-b-PBLK). The poly-β-(L)-homolysine (PBLK) performs as the bacterial-killing block and forms a left-handed helical structure; the chiral D-glucose derived PDGu block also forms secondary helical structures after deprotection and contributes to the binding of the copolymer with lipid II as shown by computer simulation. The block-like copolymer shows enhanced selectivity towards different bacteria, biocompatibility vs mammalian cells and spontaneous assembly. All these features and the in vivo studies make it a promising agent for commercial applications.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

As used herein, the term "about", in the context of temperatures, unit numbers or molecular weights, typically means +/−10% of the stated value, more typically +/−5% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

Experimental Section

Various embodiments relate to a β-peptido sugar-copolymer of Formula (I), to a process to make the β-peptido sugar-copolymer, and its medical application.

Example 1: Monomer Synthesis

The cyclic sugar derived β-lactam monomer 1 (β-lactam-D-glucose or DGu) was prepared on multigram scales in moderate yield by adopting reported methods via the stereoselective cycloaddition of tri-O-benzyl-D-glucal and chlorosulfonyl isocyanate, followed by in situ reduction to remove the sulfonyl group.

The synthesis of the monomer β-lactam-L-homolysine 2 (β-lactam-L-hLys or BLK) begins with a commercially available protected form of amino acid L-lysine, which is transformed using the Arndt-Eistert sequence to provide $\beta^3$-hLys in high yield. Then $\beta^3$-hLys was cyclized following the general procedure of Mukaiyama to generate N-Boc-β-lactam-L-hLys. Considering that benzyl groups could be removed completely from O-benzyl-PASs by Birch reduction, the N-Boc group to N-Cbz in side chain of β-lactam monomer was replaced in order to cleave both O-Bn and N-Cbz of target copolymers in one step.

Example 2: Polymer Synthesis and Characterization

Figure 2:
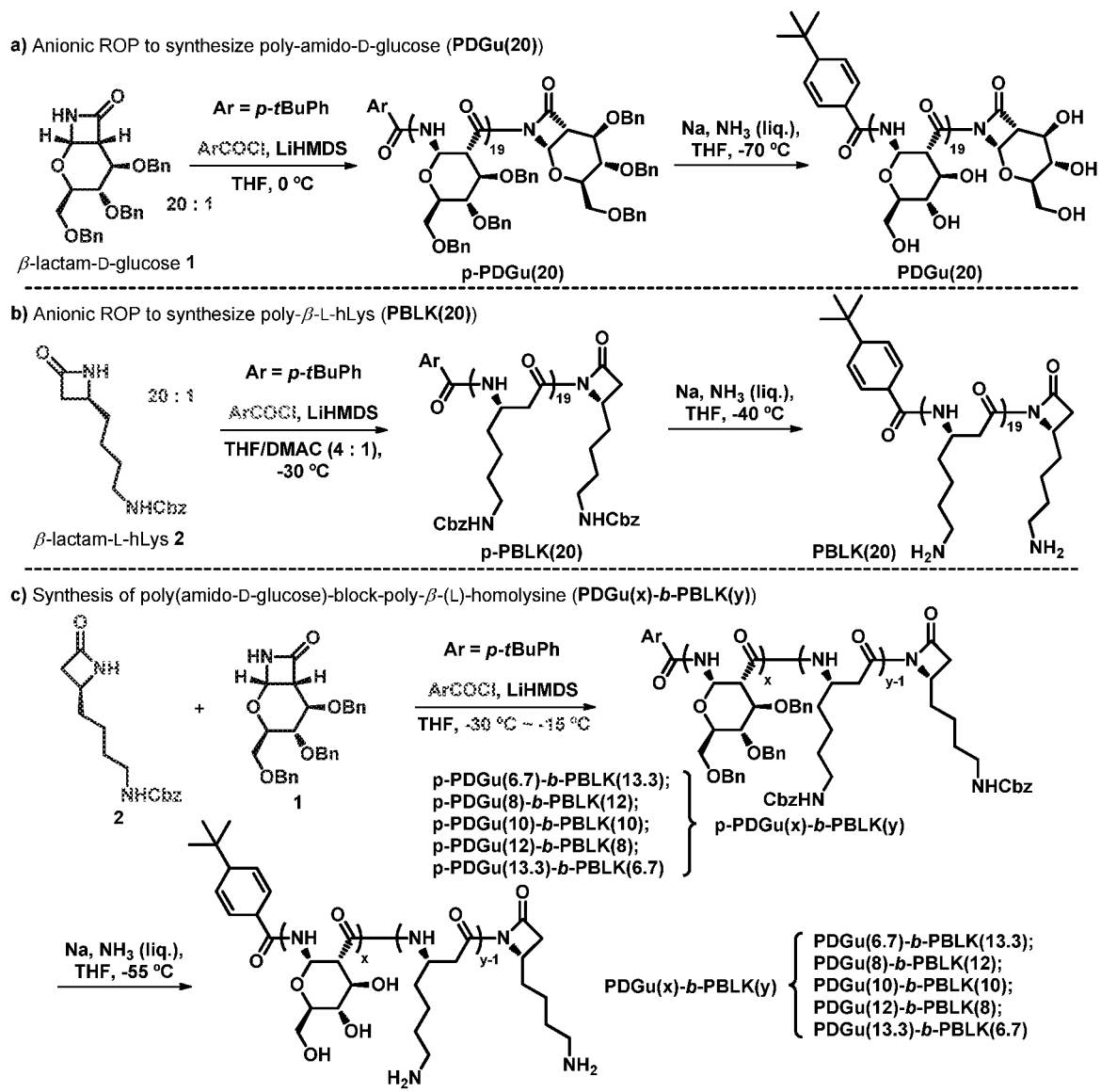
FIG. 2 shows the anionic ROP to synthesize polyamido-D-glucose (FIG. 2a), poly-β-hLys (FIG. 2b) and poly(amido-D-glucose)-block-poly-β-(L)-homolysine (FIG. 2c).

With two kinds of chiral monomers in hand, homopolymers were synthesized first. Benzoyl chloride and Lithium bis(trimethylsilyl)amide (LiHMDS) have been proven to be the appropriate initiator and base respectively, leading to yield PDGu with low dispersity and controlled length via anionic ROP of DGu 1. DGu 1 was polymerized with 5 mol % 4-tert-butylbenzoyl chloride to obtain O-Bn-poly-amido-D-glucose [p-PDGu(20), the degree of polymerization in theory $(DP_{theo})=20$]. Sodium metal in ammonia (Birch reduction) was used for the subsequent deprotection (FIG. 2a).

Gellman developed a metal-catalyzed ROP to synthesize PBLK for gene delivery with a polydispersity index (PDI) of 1.5. However, a well-controlled anionic ROP to synthesize PBLK has yet to be reported. The optimal condition is illustrated in FIG. 2b. The polymer p-PBLK(20) could be accessed with a reasonable molecular weight under a modulated method. After deprotection by using sodium in ammonia, the molecular weight of the water-soluble PBLK(20) calculated based on gel permeation chromatography (GPC) was close to the theoretical value with an acceptable dispersity (Đ=1.2).

Figure 4:
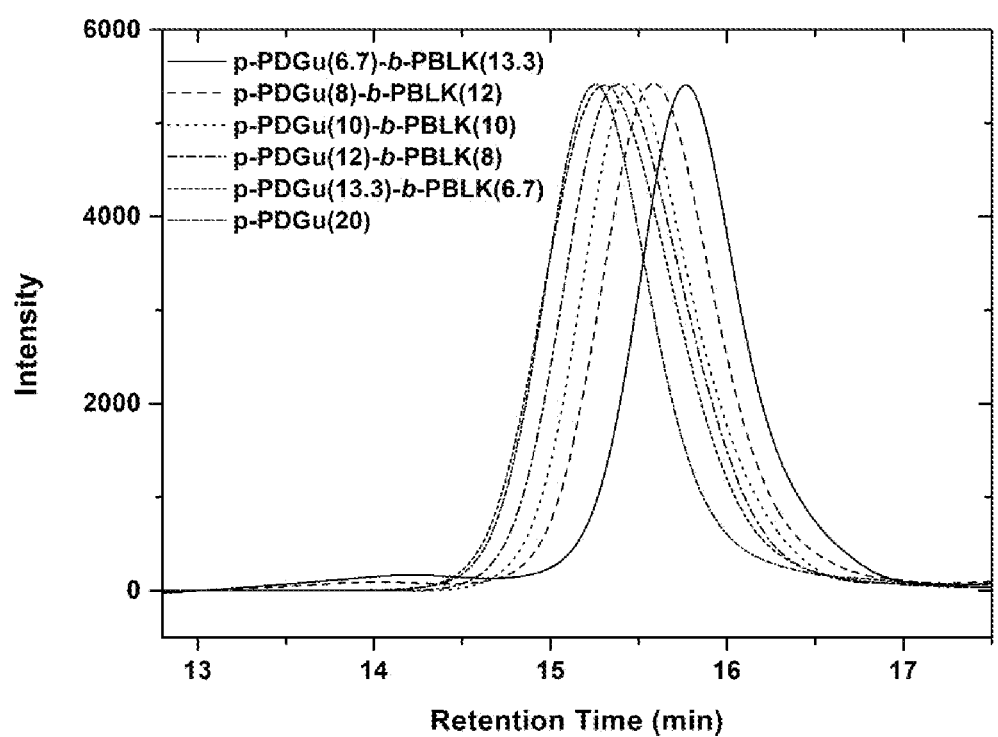
FIG. 4 shows gel permeation chromatography (GPC) of p-PDGu(x)-b-PBLK(y).

Traditional block copolymers are synthesized mostly based on the sequential addition of monomers, which increases the possibility of terminating "living" chains. Under the optimal conditions, monomers 1 and 2 were simply mixed together and polymerized with 5 mol % initiator to obtain a series of block-like copolymers poly (amido-D-glucose)-block-poly-β-(L)-homolysine with different DGu to BLK ratios (FIG. 2c, p-PDGu(x)-b-PBLK(y), with theoretical degree of polymerization (x+y)=20). The molecular weight of protected-polymers calculated based on GPC referring to polystyrene standards were close to the theoretical values with low levels of dispersity ranging from 1.08 to 1.13 (Table 1 and FIG. 4). After deprotection of the PDGu and PBLK segments, water soluble PDGu(x)-b-PBLK(y) was obtained.

Figure 5:
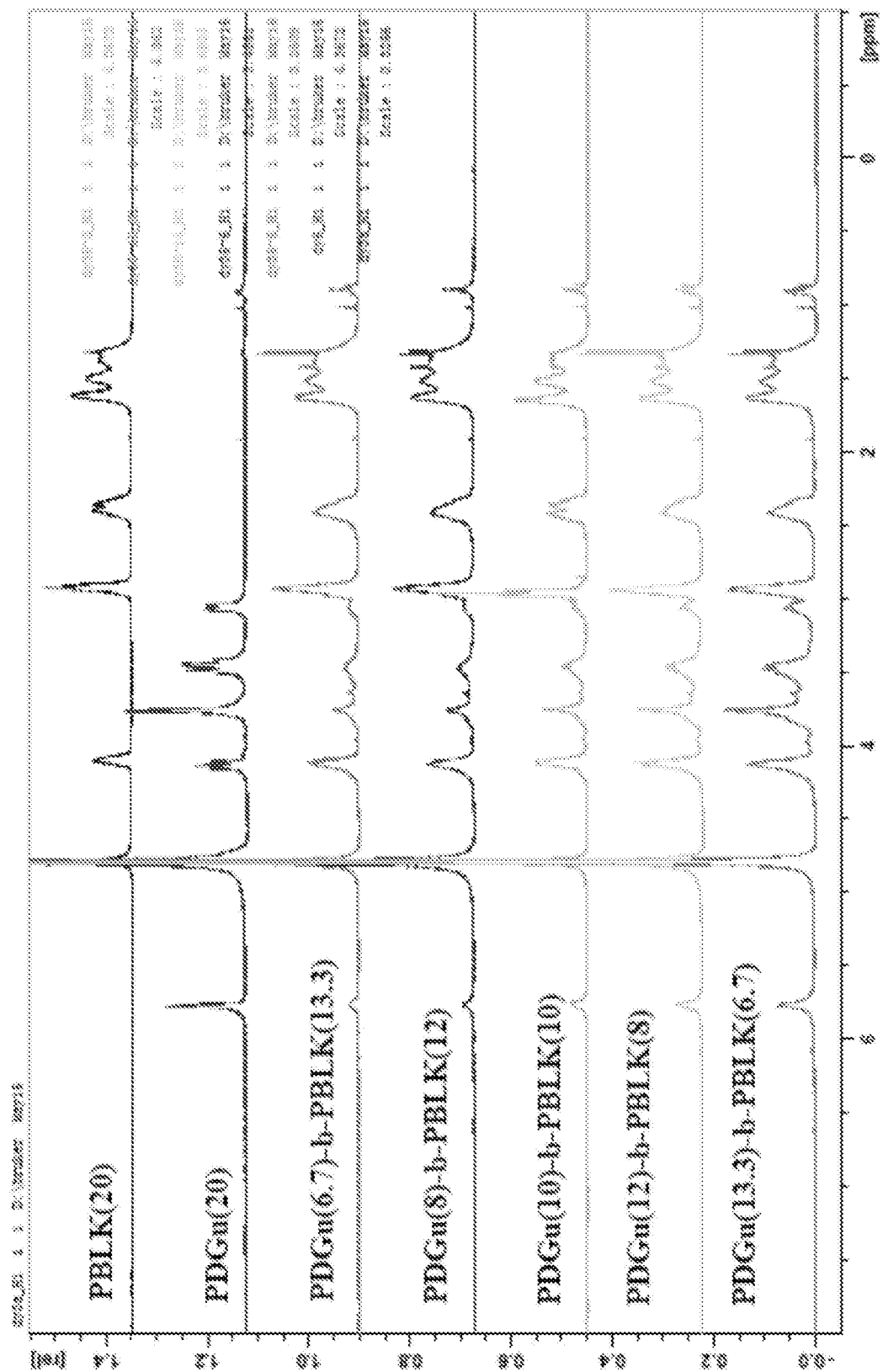
FIG. 5 shows 1H NMR of PDGu(x)-b-PBLK(y) (room temperature).
Figure 6:
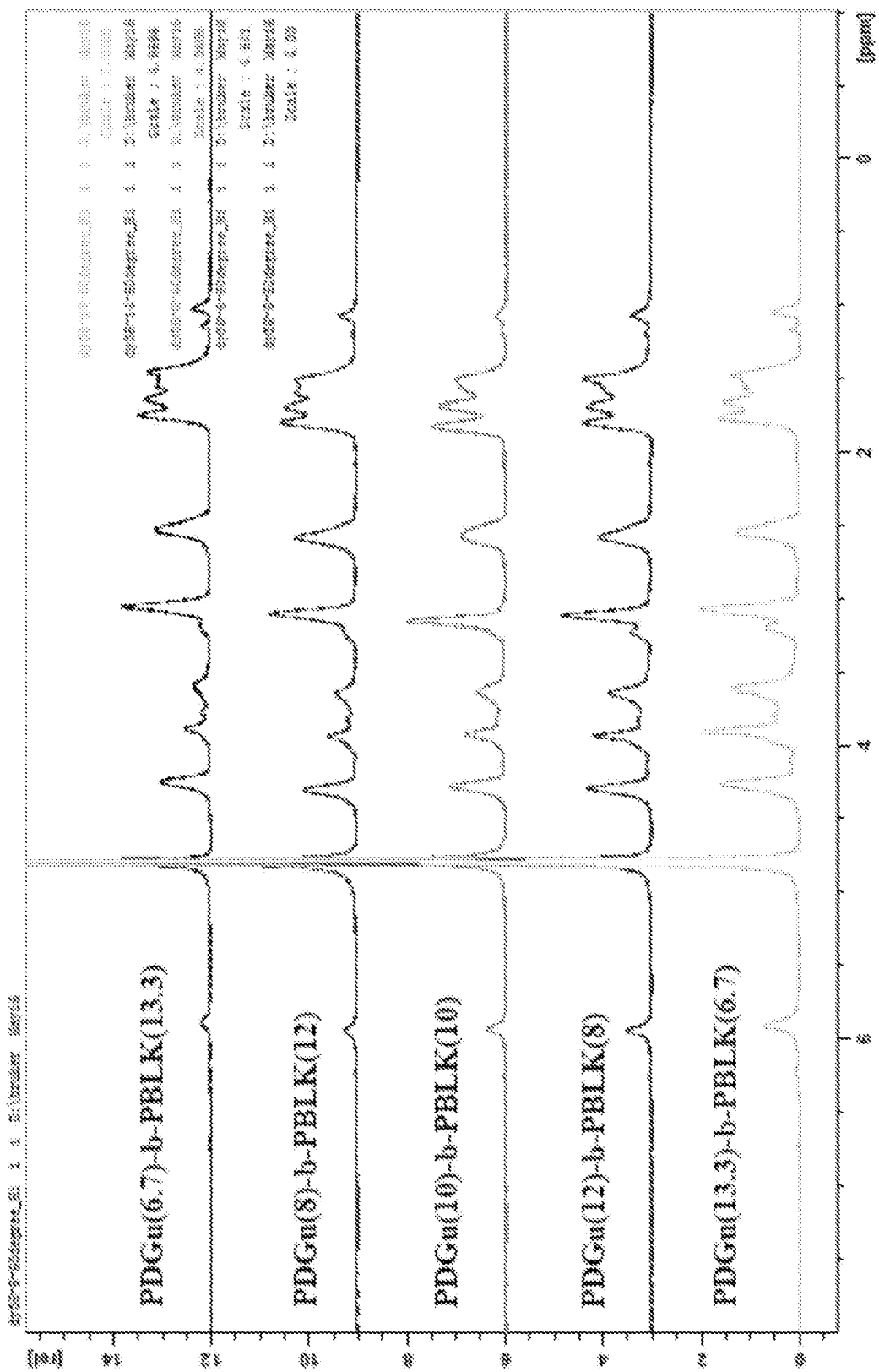
FIG. 6 shows 1H NMR of PDGu(x)-b-PBLK(y) (50° C.).

Although the molecular weights of p-PDGu(x)-b-PBLK (y) seem close to theoretical values, NMR integrations (FIGS. 5 & 6) showed that the ratios of the DGu to the BLK in the final products PDGu(x)-b-PBLK(y) are different from stoichiometric ratios of added monomers 1 and 2. For example, the actual ratio of the DGu to the BLK in PDGu (10)-b-PBLK(10) is about 1:2, that means the degree of repeated units is less than 10 in PDGu segment and more than 10 in PBLK segment. A similar trend can be seen in other samples (e.g., the actual ratio of monomers 1 to 2 in PDGu(13.3)-b-PBLK(6.7) is about 1:1). These results are repeatable after comparing different batches. Table 1 shows the molecular weights and the polydispersities of the obtained copolymers, and ratios of DGu to BLK segments in the obtained copolymers PDGu(x)-b-PBLK(y).

TABLE 1

Molecular weights and polydispersities of (co)polymers, and ratios of DGu to BLK in final products PDGu(x)-b-PBLK(y)

| Sample | $M_{n, theo}$ (Da) | $M_{n, GPC}{}^a$ (Da) | PDI[a] | Theoretical ratio of DGu to BLK | Calculated ratio[b] of DGu to BLK |
|---|---|---|---|---|---|
| PDGu$_p$(6.7)-b-PBLK$_p$(13.3) | 6913 | 6519 | 1.10 | 1:2 | 1:3 |
| PDGu$_p$(8)-b-PBLK$_p$(12) | 7151 | 6992 | 1.09 | 1:1.5 | 1:2.5 |
| PDGu$_p$(10)-b-PBLK$_p$(10) | 7518 | 7398 | 1.11 | 1:1 | 1:1.95 |
| PDGu$_p$(12)-b-PBLK$_p$(8) | 7884 | 7758 | 1.12 | 1:0.67 | 1:1.33 |
| PDGu$_p$(13.3)-b-PBLK$_p$(6.7) | 8122 | 8074 | 1.13 | 1:0.5 | 1:1 |
| PDGu$_p$(20) | 9350 | 8278 | 1.08 | — | — |

[a]$M_n$ and PDI were calculated based on GPC analysis of PDGu$_p$(x)-b-PBLK$_p$(y)
[b]Ratios were calculated based on $^1$H NMR integrations of PDGu(x)-b-PBLK(y)

The formation of left-hand $3_{14}$ helix structure of PAS was found and investigated by both circular dichroism (CD) and molecular modeling by Grinstaff. CD and computer simulations showed that polymers PDGu(x)-b-PBLK(y) adopt a sequential double-helix structure with a right handedness due to the D-glucose derived PDGu block and the opposite left handedness due to the chiral cationic PBLK block (FIG. 3). Based on the simulation results, the block peptide could have 2 different conformations: one is a right-handed 12 helical sugar segment linked with a left-handed 12 helical cationic segment (blk12-12, FIG. 3b); the other one is a right-handed 12 helical sugar segment linked with a left-handed 14 helical cationic segment (blk12-14, FIG. 3c). Helical structure could be maintained during the simulation in both cases, and compared with the segments linkage area of blk12-12, which still had H-bonds within backbone, the linkage area of blk12-14 was more like random coil. So the relative position of the two segments in blk12-14 should be much more flexible than that in blk12-12.

Example 3: Commercial Applications: Antimicrobial Activity and Cytotoxicity

Antimicrobial, hemolytic activity & MTT assay of polymers PDGu(x)-b-PBLK(y) are shown in Table 2.

TABLE 2

| Sample | PDI[a] | MIC[b] (µg/mL) | | | | | | HC$_{10}$ (µg/mL) RBC | IC$_{50}$ (µg/mL) 3T3 |
|---|---|---|---|---|---|---|---|---|---|
| | | E. coli | MRSA | SA 25923 | SA 29213 | SA USA300 | B. subtilis | | |
| PBLK(20) | — | 16 | 8 | | 8 | 8 | 4 | 5000 | 18 |
| PDGu(6.7)—b—PBLK(13.3) | 1.10 | 64 | 8 | 8 | 8 | 8 | 4 | 3300 | 100 |
| PDGu(8)—b—PBLK(12) | 1.09 | 64 | 8 | 16 | 8 | 8 | 4 | 4800 | 150 |
| PDGu(10)—b—PBLK(10) | 1.11 | 128 | 8/16 | 16 | 8 | 16 | 4 | >20 k | 430 |
| PDGu(12)—b—PBLK(8) | 1.12 | 128 | 16 | 32 | 16 | 16 | 8 | >20 k | 395 |
| PDGu(13.3)—b—PBLK(6.7) | 1.13 | 256/512 | 32 | | 32 | 32/64 | 16 | >20 k | 630 |
| PDGu(20) | 1.08 | >512 | >512 | >512 | >512 | | | >20 k | >1024 |
| Magainin 2 | — | 64 | >512 | | >512 | | | >500 | |
| LL37 | — | >512 | >512 | | >512 | | | | |
| Melittin | — | 32 | 8 | | 8 | | | 8 | |
| Polymyxin B | — | 2 | 64 | | 32 | | | >2500 | |

[a]Determined based on the GPC analysis of the Bn- and Cbz-protected polymers, using DMF (containing 1 mg/ml LiBr) as eluent and narrow polystyrene standards as reference.
[b]The strains used in this study were: E. coli (ATCC 8739), methicillin-resistant S. aureus (BAA-40), S. aureus (ATCC 25923), S. aureus (ATCC 29213), S. aureus (USA300), B. subtilis (ATCC 6633).

In the Table shown above, the values for x and y would refer to the ratio of the components as used in the synthesis. As shown in Table 1 above, these ratios differ from the actual ratios in the obtained copolymer, which are calculated based on $^1$H NMR integration.

Antimicrobial activity of block-like copolymers PDGu(x)-b-PBLK(y) against a panel of bacteria including both Gram-positive (S. aureus and B. subtilis) and Gram-negative (E. coli) in terms of minimal inhibition concentration (MIC) were tested. The polymer (PDGu(10)-b-PBLK(10)) has relatively good MICs (4-16 µg/mL) against Gram-positive bacteria, including against Methicillin-resistant Staphylococcus aureus (USA300, a community-associated MRSA species), which is superior to most AMPS. The activity was decreased with the increase of sugar ratio. This is reasonable when considering the killing domains became less.

Toxicity towards mammalian cells was another vital factor for bio-applications. The toxicity of PDGu(x)-b-PBLK(y) was measured by the inhibitory concentration causing 50% death of fibroblast (3T3) cells (IC50) using a standard MTT test. Erythrocyte compatibility assay calculating the lysis of human red blood cells (HC$_{10}$, concentration of polymers causing 10% human red blood cells lysed) was performed to characterize the in vitro biocompatibility. Results showed that the biocompatibility was increased gradually with the rise of sugar ratio. The copolymer PDGu(10)-b-PBLK(10) is non-hemolytic (<10% hemolysis) up to a concentration of 20,000 µg/mL. For the PDGu(10)-b-PBLK(10), the IC50 was 430 µg/mL, giving a therapeutic index of around 108-27.

Example 4: Animal Tests

Figure 7:
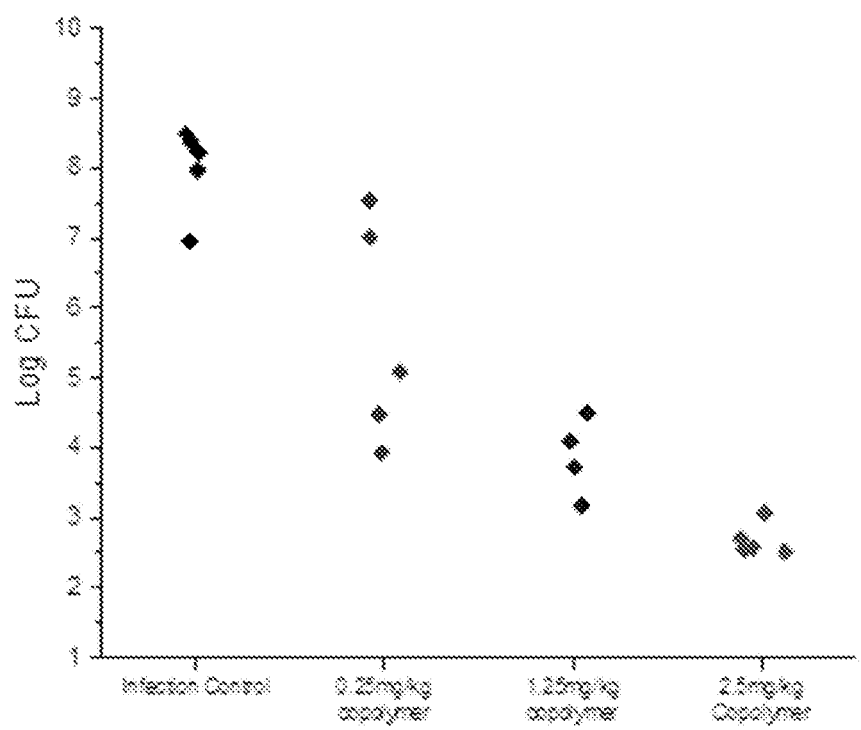
FIG. 7 shows the in vivo efficacy of PDGu(10)-b-PBLK (10) against MRSA USA300 in a mice excision wound model.

Staphylococcus aureus is the most common cause for skin and soft tissue infections (SSTIs). Among those, up to three quarter are caused by community-associated MRSA (CA-MRSA). MRSA USA300 is a significant CA-MRSA pathogen in the US. According to Centers for Disease Control and Prevention of US, 212 out of 218 MRSA isolates were type USA300. To further test the in vivo efficacy of PDGu(10)-b-PBLK(10) against the clinically significant pathogen MRSA USA300, a mice wound excision model was adopted using 8 weeks female C57BL6 mice. The β-peptido sugar-copolymer showed excellent in vivo efficacy against MRSA USA300, with a log reduction of 5.3 at dosage of 2.5 mg/kg. This could be attributed to the excellent antibacterial efficacy of the β-peptido sugar-copolymer in vivo. The killing of MRSA is dosage-dependent, as shown in FIG. 7. Although vancomycin has lower in-vitro MIC values compared with the β-peptido sugar-copolymer, it does not show superior activity during in-vivo tests.

Figure 8:
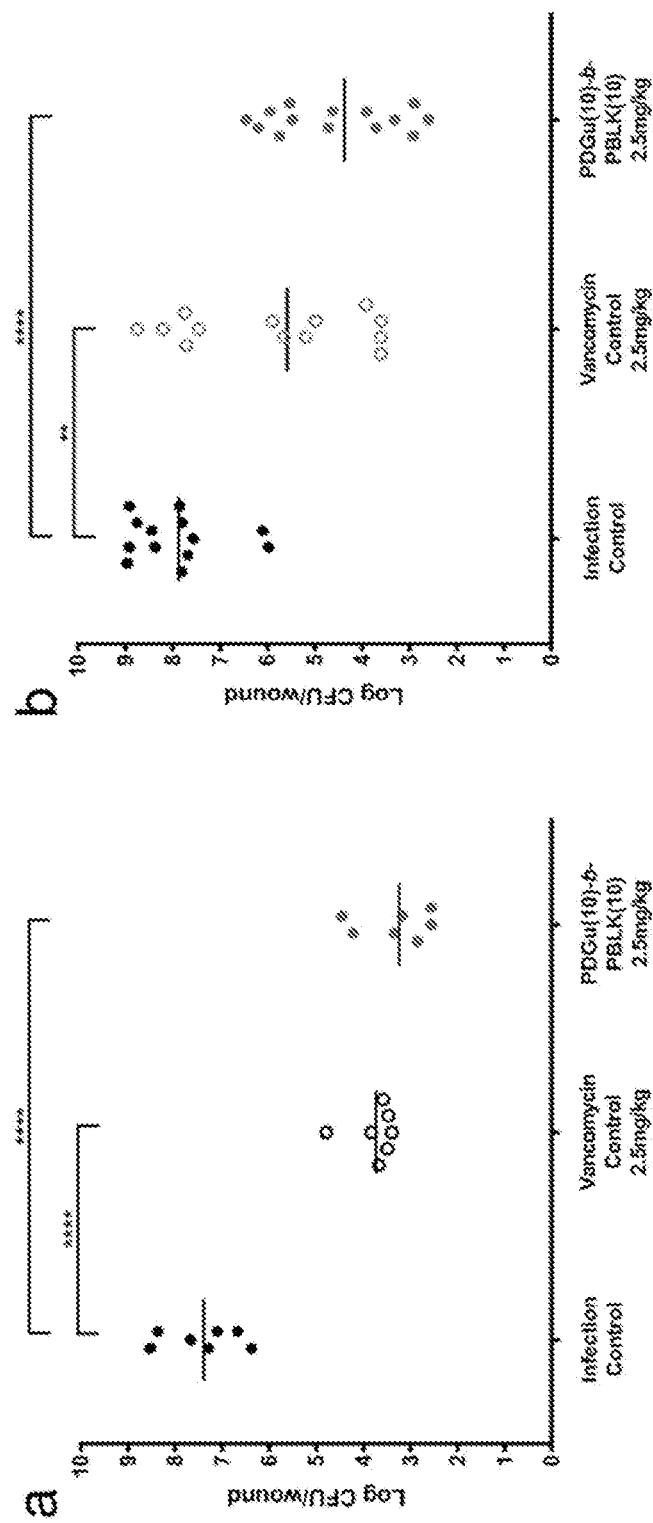
FIG. 8 shows in vivo antimicrobial activity and toxicity. (a,b) In vivo antimicrobial activity of PDGu(10)-b-PBLK (10) against MRSA USA300 in a murine excision wound model. Vancomycin control and PDGu(10)-b-PBLK(10) applied at 2.5 mg/kg. (a) Single dose treatment applied 4-hours post infection. (b) Treatment initiated 24-hours post infection and applied three times, with 4-hour interval. $p \leq 0.01$, **$p \leq 0.0001$ using one-way ANOVA followed by a Dunnett multiple comparison test.
Figure 9:
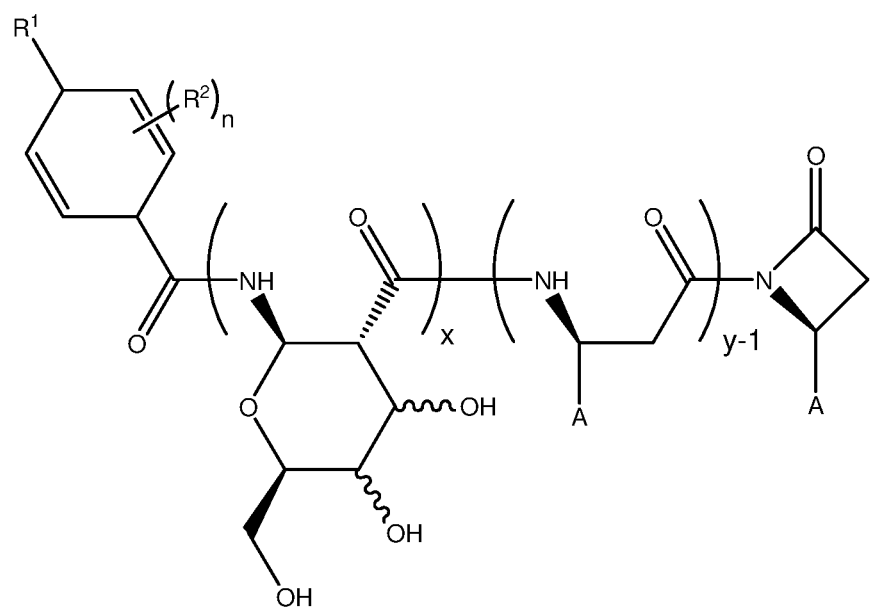
FIG. 9 shows the structure of Formula (I) as disclosed herein.

The in vivo efficacy of PDGu(10)-b-PBLK(10) was further tested against MRSA USA 300 with a murine excision wound model using two infection durations with treatments applied either 4 hour or 24 hour post infection. For treatment applied 4 hour post infection, the β-peptido sugar-copolymer achieves a log reduction of 4.1 (FIG. 8a), which is slightly better than vancomycin, which has a log reduction of 3.7. For treatment applied 24 hour post infection, by which time the wound is severely infected with biofilm bacteria, the copolymer treatment achieves a 3.4 log reduction of total bacteria count (FIG. 8b), equivalent to 99.96% killing (p≤0.0001). In contrast, vancomycin treatment only achieves 2.0 log reduction of the bacteria burden at the wound site (p≤0.01). The excellent in vivo antibacterial efficacy of PDGu(10)-b-PBLK(10) may be correlated to its outstanding in vitro killing kinetics and anti-biofilm bacteria property.

Example 5: In Vivo Murine Excisional Wound Model

Female C57BL6 mice (Invivos, Singapore) aged 8 weeks were used for excision wound model to evaluate in vivo antimicrobial efficacy of the β-peptido sugar-copolymer. All mice were housed on a 12 hour light-dark cycle at room temperature for one week prior to the experiment. Mice (n=7 per group) were anesthetized using isoflurane and hair from the back was removed with a shaver and sterile scalpel blade. The shaved area was further sterilized using 70% ethanol and a 5 mm diameter excision wound was created using a biopsy punch. In t=4 hour post infection model, 2.5 µL MRSA USA300 in PBS suspension ($5\times10^5$ CFU/mL) was added to wound site and covered by Tegaderm (3M™) to protect from contamination. Mice were subsequently put back in the cage and the infection was allowed to develop for 4 hours. Mice were anesthetized one more time and treatment solution was applied into wound site using 1 mL insulin syringe (Becton Dickinson and Company). Wound sites were covered by another layer of Tegaderm to prevent contamination. Mice were housed in individual cages to avoid fighting and disturbance to the wound site. For t=24 hour post infection model, a t.i.d treatment scheme was adopted with 4 hour interval. Bacteria was innoculated as previously; 24 hours post infection, first treatment was applied with PBS as negative control and vancomycin as antibiotic control. Afterwards, mice were put back in the cage and allowed to rest for 4 hours. $2^{nd}$ and $3^{rd}$ treatments were subsequently applied with 4 hour interval in between. Mice were sacrificed by $CO_2$ inhalation 24 hours after last treatment. Wound samples were harvested using sterile scalpel blade and placed in sterile tubes containing 900 µL PBS on ice. Wound samples were homogenized and 10-folds serial diluted in PBS to determine bacteria CFU.

For comparison of more than two groups, a one-way ANOVA followed by a Dunnett multiple comparison test was performed in Prism (GraphPad). Differences were considered to be statistically significant when $p<0.01$.

The invention claimed is:

1. A β-peptido sugar-copolymer having the following structure of formula (I):

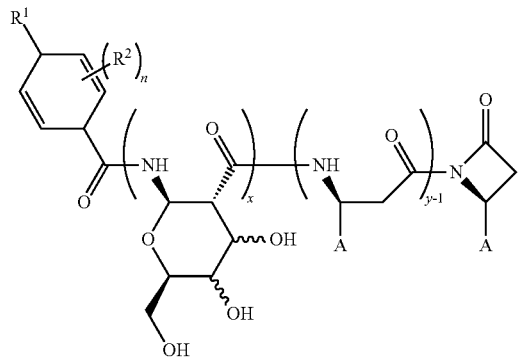

(I)

wherein:
A is selected from any amino acid residue;
x and y are independently selected from 1 to 50;
$R^1$ and $R^2$ are independently selected from the group consisting of H, a substituted or unsubstituted $C_1$-$C_{20}$ alkyl, a substituted or unsubstituted $C_1$-$C_{20}$ alkoxy, a substituted or unsubstituted $C_2$-$C_{20}$ alkenyl, a substituted or unsubstituted $C_3$-$C_{20}$ alicyclic group; and
n is an integer selected from 0 to 4;
or a stereoisomer, a tautomer, an N-oxide, a hydrate, a solvate, or a salt thereof, or a mixture of the same.

2. The β-peptido sugar-copolymer of claim 1, wherein A is selected from the group consisting of

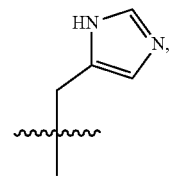 [SMILES: *Cc1cnc[nH]1]

—$(CH_2)_4$—$NH_2$ and —$(CH_2)_3$—$NHC(NH)NH_2$.

3. The β-peptido sugar-copolymer of claim 1, wherein A is —$(CH_2)_4$—$NH_2$.

4. The β-peptido sugar-copolymer of claim 1, wherein the β-peptido sugar-copolymer has the following structure of formula (II):

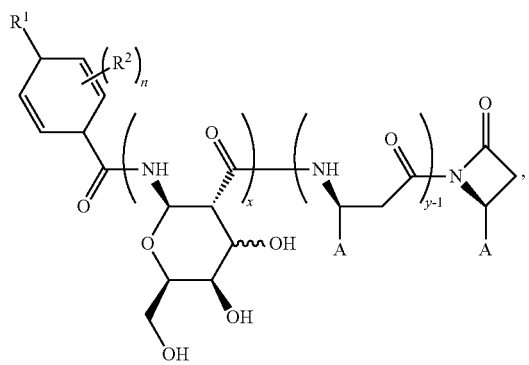

(II)

wherein $R^1$, $R^2$, A, n, x and y are as defined in claim 1, or a stereoisomer, a tautomer, an N-oxide, a hydrate, a solvate, or a salt thereof, or a mixture of the same.

5. The β-peptido sugar-copolymer of claim 1, wherein the β-peptido sugar-copolymer has the following structure of formula (III):

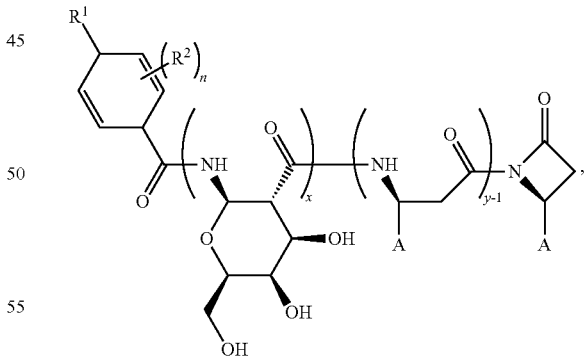

(III)

wherein $R^1$, $R^2$, A, n, x and y are as defined in claim 1, or a stereoisomer, a tautomer, an N-oxide, a hydrate, a solvate, or a salt thereof, or a mixture of the same.

6. The β-peptido sugar-copolymer of claim 1, wherein x and y are independently selected from 1 to 20.

7. The β-peptido sugar-copolymer of claim 1, wherein x and y are independently selected from 5 to 15.

8. The β-peptido sugar-copolymer of claim 1, wherein the sum of x and y is 15.

9. The β-peptido sugar-copolymer of claim 1, wherein x is about 5 and y is about 10.

10. The β-peptido sugar-copolymer of claim 1, wherein R¹ is selected from a substituted or unsubstituted $C_1$-$C_{20}$ alkyl.

11. The β-peptido sugar-copolymer of claim 1, wherein the β-peptido moiety of the copolymer forms a left-handed helical structure.

12. The β-peptido sugar-copolymer of claim 1, wherein the sugar moiety of the copolymer forms a secondary helical structure.

13. The β-peptido sugar-copolymer of claim 1, wherein the β-peptido sugar-copolymer adopts a sequential double helix structure.

14. A pharmaceutical composition comprising the β-peptido sugar-copolymer of claim 1.

15. A process for making the β-peptido sugar-copolymer of claim 1, comprising a first step of reacting a cyclic sugar derived β-lactam monomer of Formula (IV)

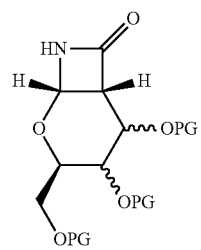

(IV)

with a β-lactam monomer of formula (V)

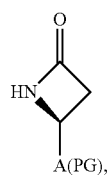

(V)

further comprising a compound of the following Formula (VI)

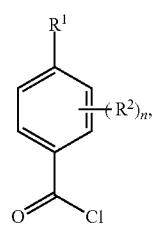

(VI)

to give a β-peptido sugar-copolymer of formula (VII)

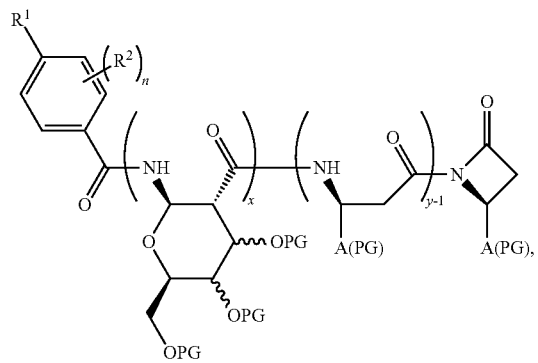

(VII)

further comprising at least one second step of deprotecting the β-peptido sugar-copolymer of Formula (VII) to give the β-peptido sugar-copolymer of Formula (I),

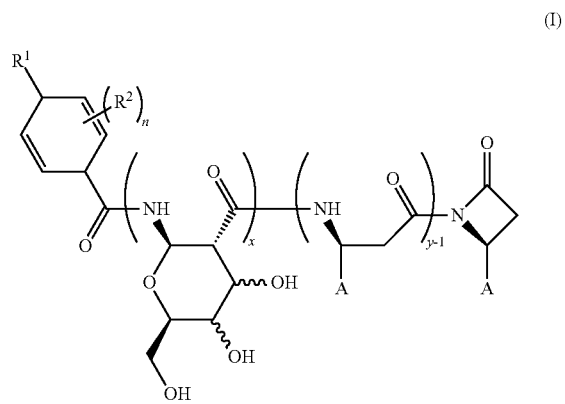

(I)

wherein PG refers to a protecting group, A(PG) refers to an optionally protected amino acid residue and A is selected from any amino acid residue;
x and y are independently selected from 1 to 50;
R¹ and R² are independently selected from the group consisting of H, a substituted or unsubstituted $C_1$-$C_{20}$ alkyl, a substituted or unsubstituted $C_1$-$C_{20}$ alkoxy, a substituted or unsubstituted $C_2$-$C_{20}$ alkenyl, a substituted or unsubstituted $C_3$-$C_{20}$ alicyclic group; and
n is an integer selected from 0 to 4.

16. The process of claim 15, wherein PG in the cyclic sugar-derived block is —Bn and PG in the amino acid-derived block is —CBz.

17. The process of claim 15, wherein all protecting groups of the β-peptido sugar-copolymer of Formula (VII) are cleaved in one step.

18. A method of treating skin and soft tissue infections comprising administering to a mammal a therapeutically effective amount of a β-peptido sugar-copolymer of claim 1.

19. The method of claim 18, wherein the therapeutically effective amount is 10 to 500 mg per day.

20. A method of treating skin and soft tissue infections comprising administering to a mammal a therapeutically effective amount of a pharmaceutical composition of claim 14.

* * * * *